(12) United States Patent
Despenic et al.

(10) Patent No.: US 11,769,591 B2
(45) Date of Patent: Sep. 26, 2023

(54) COMPUTER AIDED DIAGNOSIS AND MONITORING OF HEART FAILURE PATIENTS

(71) Applicant: KONINKLIJKE PHILIPS N.V., Eindhoven (NL)

(72) Inventors: Marija Despenic, Eindhoven (NL); Michael Alex Van Hartskamp, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 682 days.

(21) Appl. No.: 16/457,259

(22) Filed: Jun. 28, 2019

(65) Prior Publication Data
US 2020/0013510 A1    Jan. 9, 2020

(30) Foreign Application Priority Data

Jul. 6, 2018   (EP) ..................................... 18182111

(51) Int. Cl.
| | |
|---|---|
| *G16H 50/20* | (2018.01) |
| *G16H 10/60* | (2018.01) |
| *A61B 5/00* | (2006.01) |
| *G16H 50/30* | (2018.01) |
| *G16H 40/40* | (2018.01) |
| *G16H 10/20* | (2018.01) |
| *A61B 5/0205* | (2006.01) |

(52) U.S. Cl.
CPC ........... *G16H 50/20* (2018.01); *A61B 5/4884* (2013.01); *A61B 5/7282* (2013.01); *G16H 10/60* (2018.01);
(Continued)

(58) Field of Classification Search
CPC ........ G16H 50/20; G16H 10/60; G16H 10/20; G16H 40/40; G16H 50/30; A61B 5/4884;
(Continued)

(56) References Cited

U.S. PATENT DOCUMENTS

| | | |
|---|---|---|
| 7,117,030 B2 | 10/2006 | Berenfeld et al. |
| 8,888,698 B2 | 11/2014 | Bardy |

(Continued)

FOREIGN PATENT DOCUMENTS

| | | | | |
|---|---|---|---|---|
| WO | WO-2006109086 A2 | * | 10/2006 | ........... C12Q 1/6886 |
| WO | 2017032873 A2 | | 3/2017 | |

OTHER PUBLICATIONS

Inamdar, Arati A, and Ajinkya C Inamdar. "Heart Failure: Diagnosis, Management and Utilization." Journal of clinical medicine vol. 5,7 62. Jun. 29, 2016, doi:10.3390/jcm5070062 (Year: 2016).*

(Continued)

*Primary Examiner* — Evangeline Barr

(57) ABSTRACT

A system and computer program are provided for computer aided diagnosis or monitoring of heart failure patients. The system and computer program obtain patient data representing measurements of a select and limited set of health indicators of a patient. A trained classifier is applied to the patient data to obtain a classification of the occurrence or degree of heart failure for the patient. The limited set of health indicators is specifically selected from a large set of health indicators which are known to be predictive of heart failure on the basis of a clinical study which demonstrated the accuracy of the classification using this select set.

18 Claims, 5 Drawing Sheets

(52) U.S. Cl.
CPC ........... *A61B 5/0006* (2013.01); *A61B 5/0205* (2013.01); *A61B 5/7267* (2013.01); *A61B 5/7275* (2013.01); *A61B 5/7278* (2013.01); *G16H 10/20* (2018.01); *G16H 40/40* (2018.01); *G16H 50/30* (2018.01)

(58) Field of Classification Search
CPC ... A61B 5/7282; A61B 5/0006; A61B 5/0205; A61B 5/7267; A61B 5/7275; A61B 5/7278
See application file for complete search history.

(56) References Cited

U.S. PATENT DOCUMENTS

| | | | |
|---|---|---|---|
| 9,526,456 | B2 | 12/2016 | Bardy |
| 2011/0119078 | A1 | 5/2011 | Cotter et al. |
| 2011/0224565 | A1 | 9/2011 | Ong et al. |
| 2012/0283581 | A1 | 11/2012 | Olde et al. |
| 2014/0108042 | A1* | 4/2014 | Reddy ................... G16H 50/30 705/3 |
| 2014/0296675 | A1 | 10/2014 | Freeman et al. |
| 2015/0164375 | A1* | 6/2015 | Schindhelm ........... G08B 21/02 600/534 |
| 2016/0302671 | A1* | 10/2016 | Shariff ................... G16H 50/50 |
| 2016/0345854 | A1 | 12/2016 | Bardy et al. |
| 2017/0147773 | A1* | 5/2017 | Van De Stolpe ...... G16H 50/20 |
| 2017/0360310 | A1 | 12/2017 | Kiani |
| 2020/0297955 | A1* | 9/2020 | Shouldice ............. G16H 50/70 |

OTHER PUBLICATIONS

Neuberger, G., "Measures of Fatigue", Arthritis & Rheumatism, vol. 49, No. 5S, Oct. 15, 2003, pp. S175-S183.

"Heart failure", https://en.wikipedia.org/wiki/Heart_failure, Accessed Jun. 2019.

* cited by examiner

| Scenario | Accuracy | Health markers | | | | | | | |
|---|---|---|---|---|---|---|---|---|---|
| | | eGFR | BFreq | Fati | OxySat | OPNeu | Dyspnea | PFluid | GGT |
| Home diagnostic | 0.8528 | | X | X | X | X | X | | |
| Home diagnostic + laboratory tests | 0.8616 | X | X | X | X | X | X | | X |
| Home diagnostic + examination at GP clinic | 0.8591 | | X | X | X | X | X | X | |
| Home diagnostic + laboratory tests + examination at GP clinic | 0.8717 | X | X | X | X | X | X | X | X |

Fig. 3

| Scenario | Accuracy | Health markers | | | | | | | | | |
|---|---|---|---|---|---|---|---|---|---|---|---|
| | | eGFR | UR | Hmu | Fati | OxySat | OPNeu | Dyspnea | PFluid | PNeckV |
| Home monitoring | 0.7006 | | | | | | | | | |
| Home monitoring + laboratory tests | 0.7057 | x | x | | x | x | x | x | | |
| Home monitoring + examination at GP clinic | 0.7245 | | x | x | x | x | x | x | x | x |
| Home monitoring + laboratory tests + examination at GP clinic | 0.7220 | x | x | x | x | x | x | x | x | x |

Fig. 4

COMPUTER AIDED DIAGNOSIS AND MONITORING OF HEART FAILURE PATIENTS

FIELD OF THE INVENTION

The invention relates to a system and a computer program for computer aided diagnosis or monitoring of heart failure patients. The invention further relates to a workstation comprising the system, and to a computer-readable medium comprising (non)-transitory data representing the computer program.

BACKGROUND OF THE INVENTION

Heart failure is a common, costly, chronic and potentially fatal condition. For example, in 2015 it affected about 40 million people globally. In developed countries, around 2% of adults have heart failure and in those over the age of 65, the occurrence of heart failure increases to 6-10%. This is similar to the risks with a number of types of cancer. For example, in the United Kingdom, heart failure is the reason for 5% of emergency hospital admissions.

In heart failure, the heart is losing pump power. The heart is the driving force in the circulatory system, but it shares the responsibility for sufficient organ perfusion with the kidneys. Changes in cardiac performance are compensated by the kidneys. One of these compensatory mechanisms is to retain fluid to upregulate blood volume. This changes the hemodynamic status of the patient.

The American Heart Association (AHA)/American College of Cardiology guidelines defines heart failure as "a complex clinical syndrome that can result from any structural or functional cardiac disorder that impairs the ability of the ventricle to fill with or eject blood". There is no single diagnostic test for heart failure. Rather, heart failure comes with a large collection of signs and symptoms. This complicates the diagnosis of heart failure as well as the monitoring of heart failure patients for exacerbations. Currently, heart failure is clinically diagnosed based on a careful review of patient history and physical examination taking into account measurements of health indicators such as those listed in Table 1 below.

These health indicators are either directly or indirectly indicative of changes in the hemodynamic status of the patient. Some of them are easy to (subjectively) assess, such as fatigue. Others require an assessment by a trained physician, a laboratory test or diagnostic imaging.

TABLE 1

Type of measurements for the health indicators

| Health indicator | Type of measurement |
| --- | --- |
| estimated glomerular filtration rate in ml/min | Calculation/In-vitro diagnostic test, based on Creatinine level |
| Creatinine level in micro-mol/l | In-vitro diagnostic test |
| Na+ concentration mmol/l | In-vitro diagnostic test |
| Beating Frequency in beats/min | Vital signs |
| Pulse Pressure in mm Hg | Calculation/Vital signs, based on difference between the systolic and diastolic pressure readings |
| Systolic BloodPressure in mm Hg | Vital signs |
| Heart Rhythm | Vital signs |
| Heart Sound | Physical examination |
| Enlarged Heart | Scan |
| Fatigue | Questionnaire |
| Dyspnea in breaths/min | Examination/Questionnaire |
| Heart Murmur | Physical examination |
| Urea in mmol/l | In-vitro diagnostic test |
| Aspartate Transaminase in IU/l | In-vitro diagnostic test |
| Oxygen Saturation in % | Vital signs/In-vitro diagnostic test |
| Orthopnea | Questionnaire |
| Pleura Fluid | Physical examination |
| Gamma-glutamyl transpeptidase in IU/l | In-vitro diagnostic test |
| Liver tender enlargement in cm | Physical examination/Scan |
| Nausea | Questionnaire |
| Prominent neck veins, cm above sternal angle | Physical examination |
| Pitting Edema - symmetrical ankle/pretibial | Physical examination |
| Pitting Edema - sacral (night) | Physical examination |
| Nocturia/times going to toilet per night | Questionnaire |
| Heart Sound Tricuspedalic valve | Physical examination |
| Brain natriuretic peptide in pg/mL | In-vitro diagnostic test |
| Weight Gain kg/day | Measurement |

Table 1 indicates the types of measurements needed for the measurement of the respective health indicators. Here and in the following, the term 'measurement' is to be understood as referring to the assignment of a number or other quantitative value to a phenomenon according to a rule. More specifically, the types of measurements may be categorized in several categories:

In-vitro diagnostic test: In-vitro diagnostic test represents a biomarker measurement in a body fluid, such as blood. In general, this is measured in a central laboratory, but may also be measured at home. Such measurements may also be ordered in desired intervals by caregivers and blood may be drawn at community health centers or outpatient clinics.

Vital signs: Vital signs may be measured by an expert but may also be measured at home if suitable measurement device(s) are available.

Physical examination is performed by an expert, e.g., at the hospital or at a General Practitioner's (GP) clinic, and typically cannot be performed at home without aid/guidance (e.g., by a medical device).

Scan: Different scans—CT, US, X-Ray, etc. are typically acquired in a hospital, and normally not at home or in a GP's clinic.

Questionnaire is a list of questions which is filled in by a patient. Therefore, this type of measurement may be performed at home.

Examination represents a simple examination by an expert, which may also be done at home with proper aid/guidance, e.g., by medical device.

Measurement is a simple/direct measurement that may be done at home.

Diagnosing or monitoring heart failure using the large set of health indicators requires significant expertise in cardiology. This expertise is scarce. In developed countries, the number of patients is increasing fast. In developing countries there are only very few trained cardiologists for a large and growing population. Alternatives are being sought in telemonitoring or tele-diagnosis.

Currently, it is still too difficult for regular healthcare professionals to treat outpatients given the large set of health indicators. This makes it nearly impossible to diagnose heart failure patients in more isolated areas where specialists are hours travel away or even to monitor heart failure patients at home.

Specifically, many health indicators are currently considered as necessary for diagnosis of a heart failure. This makes diagnosis expensive, and in particular outpatient diagnosis very expensive because additional medical (measurement) devices, tools or methods are needed to measure these health indicators, while some cannot even be measured without sufficient expertise.

The above also applies to monitoring of heart failure, although here the opposite is also known, namely that only very few health indicators are used for monitoring which makes selecting patients for referral to a specialist error prone.

SUMMARY OF THE INVENTION

It would be advantageous to obtain a system and computer program for computer aided diagnosis or monitoring which is sufficiently accurate but which is less complex (and thereby costly) to perform and/or better suited for outpatient use.

The following measures essentially provide computer aided diagnosis or monitoring of heart failure using a select and limited set of health indicators. The set has been identified as being surprisingly accurate, yet relatively simple to measure and in view of the types of measurements, well-suited for outpatient use.

In accordance with a first aspect of the invention, a system is provided for computer aided diagnosis or monitoring of heart failure patients, the system comprising:

a memory comprising instruction data representing a set of instructions, and classifier data representing a classifier;

a processor configured to communicate with the memory and to execute the set of instructions, wherein the set of instructions, when executed by the processor, cause the processor to:

obtain patient data representing measurements of a select set of health indicators of a patient, the select set of health indicators comprising fatigue level of the patient, orthopnea of the patient, dyspnea of the patient, and oxygen saturation of the patient;

retrieve the classifier from the memory, wherein the classifier is trained on training data, wherein each sample of the training data represents the measurements of the select set of health indicators of a studied patient and has a label indicating an occurrence or degree of heart failure of the studied patient;

apply the classifier to the patient data to obtain a classification of the occurrence or degree of heart failure for the patient; and generate output data representing the classification.

In accordance with a further aspect of the invention, a workstation and server are provided comprising the system.

In accordance with a further aspect of the invention, a computer readable medium is provided comprising transitory or non-transitory data representing a classifier trained on training data and having as input measurements of a select set of health indicators of a patient and as output a label indicating an occurrence or degree of heart failure of the patient, the select set of health indicators comprising fatigue level, orthopnea, dyspnea and oxygen saturation of the studied patient.

In accordance with a further aspect of the invention, a computer program is provided which comprises instructions which, when executed by a processor system, cause the processor system to carry out a computer aided diagnosis or monitoring of heart failure patients by:

accessing patient data representing measurements of a select set of health indicators of a patient, the select set of health indicators comprising fatigue level of the patient, orthopnea of the patient, dyspnea of the patient, and oxygen saturation of the patient;

accessing a classifier trained on training data, wherein each sample of the training data represents the measurements of the select set of health indicators of a studied patient and has a label indicating an occurrence or degree of heart failure of the studied patient;

applying the classifier to the patient data to obtain a classification of the occurrence or degree of heart failure for the patient; and generating output data representing the classification.

In accordance with a further aspect of the invention, a computer-readable medium is provided comprising transitory or non-transitory data representing the computer program.

The above measures involve obtaining patient data representing measurements of a select set of health indicators (or 'markers') of a patient. The set of health indicators is selected to be limited in size and to specifically comprise the following health indicators: fatigue level of the patient, orthopnea of the patient, dyspnea of the patient, and oxygen saturation of the patient. The set of health indicators is specifically selected from a large set of health indicators which are known to be predictive of heart failure on the basis of a clinical study which demonstrated the accuracy of the classification using this select set.

Namely, the select set of health indicators, despite its small size and lack of complexity of measurement, is predictive of the occurrence of heart failure and/or the degree of heart failure. A clinical study, which was carried out by the inventors, has shown that a classifier trained for such types of health indicators and having accompanying labels indicating the degree of heart failure obtained an accuracy of 70.06% whereas a classifier trained on the full set of health indicators of Table 1 only provides a marginal improvement of the accuracy to 72.58%. Here and elsewhere, the cited accuracy is an average accuracy of such a classifier having been trained using five different training techniques, namely Support Vector Machines (SVM) with linear kernel, Logistic Regression, Random Forest, Gradient Boosting Machine and Stochastic Gradient Descent, with the training involving a Leave One (Patient) Out cross-validation of the training data to improve assessment of the generalization of the classification.

The select set of health indicators is relatively simple to measure, including, for example, in an outpatient setting. For example, fatigue may be measured through a questionnaire and quantified as none, some or severe fatigue. Orthopnea may also be evaluated based on a questionnaire, for example, by questioning whether someone uses pillows during night, and if so, how many. Dyspnea is a breathing frequency in breaths/min which may be measured by examination/questionnaire. Oxygen saturation (in %) of a patient may be measured by a measurement device, such as a pulse oximeter. All of the above health indicators may thus be measured at home, requiring only a measurement device for the measurement of the oxygen saturation.

In accordance with the above measures, a system and computer program are provided which use this select set of health indicators to arrive at a classification by means of a trained classifier. The classifier is trained on training data comprising measurements of the same health indicators and accompanying labels, being either an occurrence of heart failure in case of computer aided diagnosis or a degree of heart failure in case of computer aided monitoring. Such training data may be obtained from a clinical study or from clinical databases, with the labels being typically assigned manually by clinical experts. Suitable trained classifiers include, but are not limited to, those trained using Support Vector Machines (SVM) with linear kernel, Logistic Regression, Random Forest, Gradient Boosting Machine and Stochastic Gradient Descent. Optionally, a Leave One Patient Out cross-validation of the training data may be performed so as to improve assessment of the generalization of the classification by the classifier.

During use, the classifier is retrieved by the system from memory and applied to the patient data to obtain a classification of the occurrence or degree of heart failure of the patient. Here, the classification of the occurrence of heart failure may be a binary classification (e.g., 'heart failure' or 'no heart failure') but may also express a likelihood of heart failure (e.g., '80%') or confidence in the classification. The system and computer program generate output data representing the classification, which may for example be output data representing a visual or auditive rendering of the classification, output data representing a part of a report which provides the classification, etc. The system and computer program thus provide an accurate classification of heart failure on the basis of health indicators which are simple to measure. Advantageously, the system and the computer program are well-suited for outpatient use.

Optionally, the system further comprises:
a user input interface configured to receive user input data from a user input device operable by a user; and
a display output interface configured to provide display data to a display to visualize output of the system;

and wherein the processor is configured to communicate with the user input interface and the display output interface, wherein the set of instructions, when executed by the processor, cause the processor to:
using the user input interface and the display output interface, establish a user interface which enables a user to provide information indicative of at least one of the fatigue level, the orthopnea and the dyspnea of the patient by providing answers to one or more onscreen questions;
using a rule-based system, determine a respective one of the measurement of the fatigue level, the measurement of the orthopnea and the measurement of the dyspnea of the patient based on the answers provided to the one or more onscreen questions.

Fatigue level, orthopnea and dyspnea may be measured by questionnaire, with the term 'questionnaire' referring to one or a set of questions, which are devised such that the answers to these questions are indicative of a respective health indicator. The use of questionnaires for assessing these types of health indicators is known per se. For example, for fatigue, "*Measures of Fatigue*" by Neuberger et al., Arthritis & Rheumatism, Vol. 49, No. 5S, Oct. 15, 2003, pp. S175-S183, describes such questionnaire. To effectively translate the answers to a measurement of the respective health indicator, a rule-based system is used which provides an interpretation of the answers and thereby the measurement. Here, the term 'ruled-based system' refers to any system which is suitable to interpret the answers and translate them to measurement values, including but not limited to heuristically designed rules but also expert systems. The user is enabled to take the questionnaire using the user interface. It is therefore not needed for the user to use separate (e.g., paper-based) questionnaires or measurement devices to measure these health indicators.

Optionally, the system comprises an interface to a measurement device for obtaining the measurement of the oxygen saturation of the patient. The oxygen saturation of the patient is normally measured using a measurement device. By providing a data interface to the measurement device, e.g., via Bluetooth, ZigBee or any other data interface, it is not needed for the user to manually input the measured oxygen saturation. This may avoid transcription errors. Alternatively, the oxygen saturation may be input via the user interface.

In an embodiment, the system is configured for computer aided diagnosis, the classifier is trained using the occurrence of heart failure as label for each training sample, and the select set of health indicators further comprises the beating frequency of the patient. It has been found in the aforementioned clinical studies that specifically for computer aided diagnosis of the presence of heart failure, the select set of health indicators with beating frequency as an additional health indicator is well-suited to predict the presence of heart failure. Namely, a classifier trained for such types of health indicators and having accompanying labels obtained an accuracy of 85.28% whereas a classifier trained on the full set of health indicators of Table 1 only provides a marginal improvement of the accuracy to 86.92%.

Optionally, the select set of health indicators consists of the fatigue, the orthopnea, the dyspnea, the oxygen saturation and the beating frequency of the patient. In view of the accuracy and the relative ease of measuring the health indicators, it may, for example, for at-home use, suffice to use the claimed set of five health indicators, thereby refraining from using further health indicators. This enables diagnosis of heart failure without the use of laboratory tests and/or without requiring examination at a GP's clinic.

Optionally, the select set of health indicators further comprises, at the most, one or more of:
estimated glomerular filtration rate of the patient;
gamma-glutamyl transpeptidase level of the patient; and
pleural fluid of the patient.

The aforementioned health indicators may provide smaller improvements to the accuracy of the diagnosis, albeit with health indicators which may require laboratory tests and/or examination at a GP's clinic to obtain their measurement. Nevertheless, of the full set of health indicators of Table 1, these health indicators have been found to provide most additional predictive quality when supplementing the aforementioned select set of health indicators.

In an embodiment, the system is configured for computer aided monitoring, and the classifier is trained using the degree of heart failure as label for each training sample. As mentioned earlier, the select set of health indicators may consist of the fatigue level, the orthopnea, the dyspnea and the oxygen saturation of the patient, which enables monitoring of heart failure without the use of laboratory tests and/or without requiring examination at a GP's clinic Optionally, the select set of health indicators further comprises, at the most, one or more of:
estimated glomerular filtration rate of the patient;
urea level of the patent;
pleural fluid of the patient; and
size of prominent neck veins of the patient.

The aforementioned health indicators may provide smaller improvements to the accuracy of the monitoring, albeit with health indicators which may require laboratory tests and/or examination at a GP's clinic to obtain their measurement. Nevertheless, of the full set of health indicators of Table 1, these health indicators have been found to provide most additional predictive quality when supplementing the aforementioned select set of health indicators.

It will be appreciated by those skilled in the art that two or more of the above-mentioned embodiments, implementations, and/or optional aspects of the invention may be combined in any way deemed useful.

Modifications and variations of the workstation, the computer program and/or the computer-readable medium which correspond to the described modifications and variations of the system, can be carried out by a person skilled in the art on the basis of the present description.

BRIEF DESCRIPTION OF THE DRAWINGS

These and other aspects of the invention will be apparent from and elucidated further with reference to the embodiments described by way of example in the following description and with reference to the accompanying drawings, in which

FIG. 3 shows a table with select sets of health indicators for the diagnosis of heart failure in different diagnosis scenarios and the average normalized accuracies of five classifiers using the selected health indicators;

FIG. 4 shows a table with select sets of health indicators for the monitoring of heart failure in different monitoring scenarios and the average normalized accuracies of five classifiers using the selected health indicators;

It should be noted that the figures are purely diagrammatic and not drawn to scale. In the figures, elements which correspond to elements already described may have the same reference numerals.

LIST OF REFERENCE NUMBERS

Figure 1:
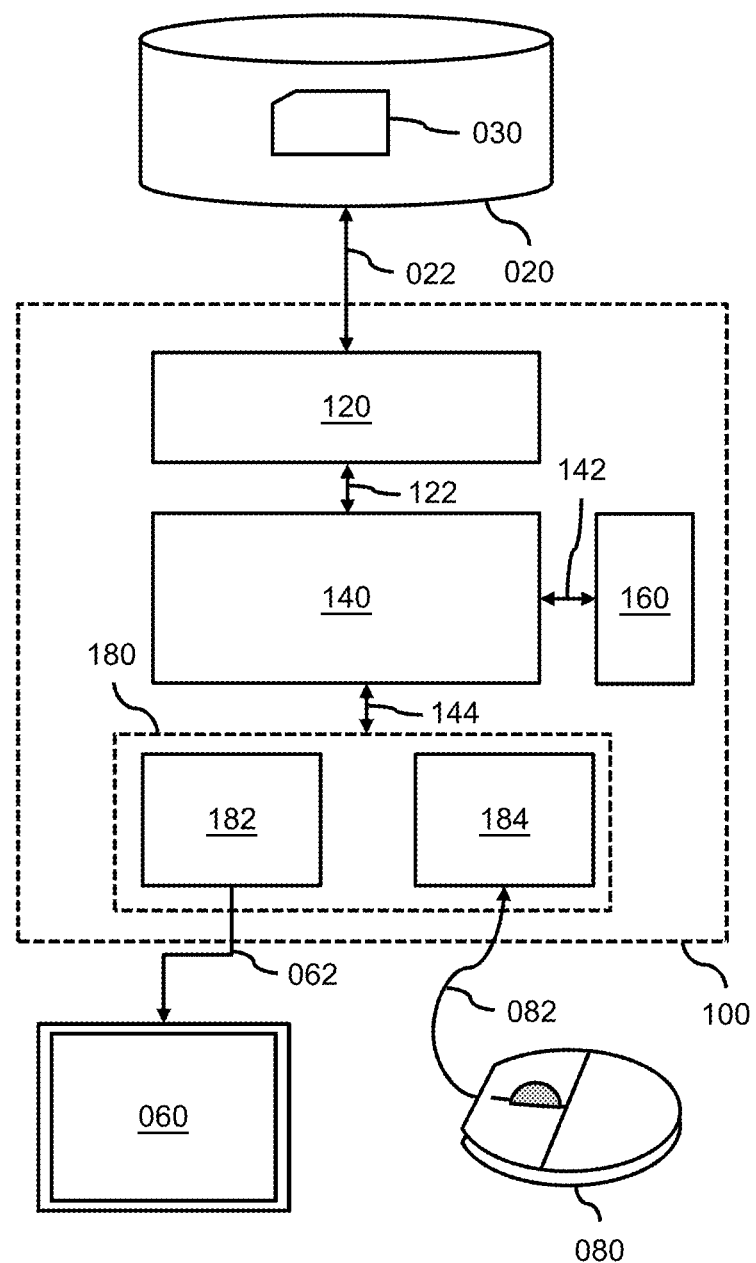
FIG. 1 shows a system for computer aided diagnosis or monitoring of heart failure patients which is configured to provide a user interface to a user.

The following list of reference numbers is provided for facilitating the interpretation of the drawings and shall not be construed as limiting the claims.

020 data storage
022 data communication
030 patient data
060 display
062 display data
080 user input device
082 user input data
100 system for computer aided diagnosis or monitoring
120 data interface
122 internal data communication
140 processor
142 internal data communication
144 internal data communication
160 memory
180 user interface subsystem
182 display output interface
184 user input interface
200 data flow diagram
210 measurement using measurement device
212 measurement data
220 laboratory test and questionnaire
222 questionnaire data
224 laboratory test data
230 clinical expert
232 examination data
240 mobile device
250 patient data
260 workstation
300 method for computer aided diagnosis or monitoring
310 accessing patient data
320 accessing classifier trained on training data
330 applying classifier to patient data
340 generating output data representing classification
400 computer-readable medium
410 non-transitory data

DETAILED DESCRIPTION OF EMBODIMENTS

FIG. 1 shows a system 100 for computer aided diagnosis or monitoring of heart failure patients. The system 100 comprises a memory 160 comprising instruction data representing a set of instructions, and classifier data representing a classifier. The system 100 further comprises a processor 140 configured to communicate with the memory 160 and to execute the set of instructions.

The processor 140 may be configured to, during operation of the system 100, obtain patient data 030 representing measurements of a select set of health indicators of a patient, to retrieve the classifier from the memory 160, to apply the classifier to the patient data 030 to obtain a classification of the occurrence or degree of heart failure for the patient, and to generate output data representing the classification. As will be explained with further reference to FIGS. 3 and 4, the select set of health indicators may comprise or consist of a fatigue level of the patient, orthopnea of the patient, dyspnea of the patient, and oxygen saturation of the patient. As will also be further explained with reference to FIGS. 3 and 4 and elsewhere, the classifier may be trained on training data, with each sample of the training data representing the measurements of the select set of health indicators of a 'training data' patient, and with each sample the training data having a label ('being labeled') indicating an occurrence or degree of heart failure of said patient.

There are various options for obtaining the patient data 030 to be classified. For example, as also shown in FIG. 1, the patient data 030 may be stored in a data storage 020, which is shown in the example of FIG. 1 to be an external data storage. The system 100 may obtain access to the patient data 030 via a data interface 120 and external data communication 022. Alternatively, the patient data 030 may be accessed from an internal data storage of the system. The data interface 120 may take various forms, such as a network interface to a local or wide area network, e.g., the Internet, a storage interface to an internal or external data storage, etc. The data storage 020 may take any known and suitable form.

In some embodiments, the patient data 030 stored in the data storage 020 may be generated outside of the system 100, e.g., by another system or device. For example, as also elucidated with reference to FIG. 2, the patient data 030 may be obtained by a mobile device and provided to the system 100, e.g., via a network.

In other embodiments, the patient data 030 may be generated by the system 100 and stored in an internal data storage, for example a memory such as the memory 160. For example, the patient data 030 may be generated by the system 100 on the basis of user input provided by a user via a user interface. For example, the user interface may enable the user to provide information indicative of at least one of the fatigue level, the orthopnea and the dyspnea of the patient by providing answers to one or more onscreen questions, and the processor 140 may use a rule-based system to determine a respective one of the measurement of the fatigue level, the measurement of the orthopnea and the measurement of the dyspnea of the patient based on the answers provided to the one or more onscreen questions. This aspect will be further elucidated with reference to FIGS. 3 and 4 and elsewhere.

To enable the user to provide such and similar type of user input via the user interface, the system 100 is shown to comprise a user interface subsystem 180 which may be configured to, during operation of the system 100, enable a user to interact with the system 100, for example using a graphical user interface. The user interface subsystem 180 is shown to comprise a user input interface 184 configured to receive user input data 082 from a user input device 080 operable by the user. The user input device 080 may take various forms, including but not limited to a computer mouse, touch screen, keyboard, microphone, etc. By way of example, FIG. 1 shows the user input device to be a computer mouse 080. In general, the user input interface 184 may be of a type which corresponds to the type of user input device 080, i.e., it may be a thereto corresponding type of user device interface 184.

The user interface subsystem 180 is further shown to comprise a display output interface 182 configured to provide display data 062 to a display 060 to visualize output of the system 100. In the example of FIG. 1, the display is an external display 060. Alternatively, the display may be an internal display.

In some embodiments, the user interface established by the system 100 may be or may comprise a graphical user interface which is shown on the display 060. For that purpose, the processor 140 may be configured to generate the display data 062 to display graphical elements of the graphical user interface to a user. The graphical user interface may be represented by a set of interface instructions stored as data in a memory accessible to the processor 140, being for example the memory 160 or another memory of the system 100. It is noted that, in other embodiments, the user interface established by the system 100 is not a graphical user interface. For example, the user may use a keyboard to provide text-based input to the system 100 in a text-based interface. Such a configuration of the system 100 may conventionally not be understood as a graphical user interface.

There are also various options for generating output data representing the classification. For example, the display output interface 182 may be used to display the classification on-screen to a user. Another example is that the output data may represent (part of) a file or other computer resource for recording data. In a specific example, the output data may represent part of an electronic report.

Various details and other aspects of the operation of the system 100 will be further elucidated with reference to FIGS. 3 and 4.

Figure 2:
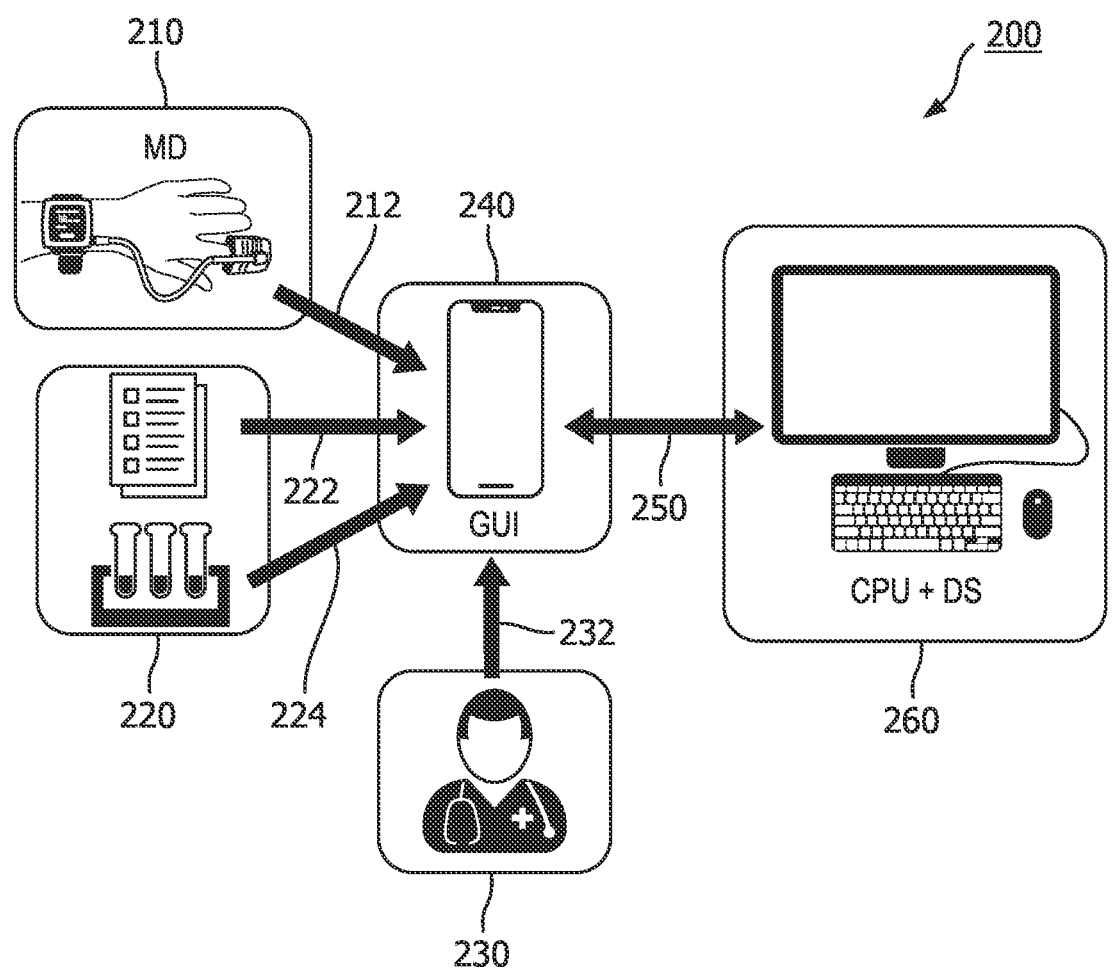
FIG. 2 shows possible data flow in the computer aided diagnosis or monitoring of heart failure patients involving a mobile device and a workstation.

In general, the system 100 may be embodied as, or in, a single device or apparatus, such as a workstation, e.g., laptop or desktop-based, or a mobile device. The device or apparatus may comprise one or more microprocessors which execute appropriate software. The software may have been downloaded and/or stored in a corresponding memory, e.g., a volatile memory such as RAM or a non-volatile memory such as Flash. Alternatively, the functional units of the system, e.g., the data interface, the user input interface, the display output interface and the processor, may be implemented in the device or apparatus in the form of programmable logic, e.g., as a Field-Programmable Gate Array (FPGA). In general, each functional unit of the system may be implemented in the form of a circuit. It is noted that the system 100 may also be implemented in a distributed manner, e.g., involving different devices or apparatuses. For example, the distribution may be in accordance with a client-server model, e.g., using a server and a thin-client, or as a mobile device providing the user interface and as a workstation receiving the patient data from the mobile device and applying the classifier to the patient data FIG. 2 shows a data flow diagram 200 for the abovementioned example of a mobile device and a workstation. Namely, here, a mobile device 240 is configured to provide a graphical user interface (labeled 'GUI' in FIG. 2) to enable measurements of the select set of health indicators to be input. Such measurements may, for example, include measurement 210 of the oxygen saturation by a measurement device (labeled 'MD' in FIG. 2). The resulting measurement data 212 may be manually input via the graphical user interface, or alternatively may be provided via a data interface to the mobile device 240. Other measurements may include laboratory tests and questionnaires, resulting in questionnaire data 222 and laboratory test data 224. The questionnaire data may represent answers to one or a set of questions. The questionnaire may be presented to the user via the graphical user interface. Alternatively, the questionnaire may be a paper-based questionnaire, with the answers being subsequently input via the graphical user interface. Other measurements may include examination data 232 obtained from examination by a clinical expert 230, which may also be input via the graphical user interface.

Having obtained the measurements of the select set of health indicators, the mobile device 240 may provide these as patient data 250 to a workstation 260 (labeled 'CPU+DS' in FIG. 2 referring to a processor and a data storage), which may then apply a classifier to the patient data 250 to obtain a classification of heart failure if configured for diagnosis, or a degree of heart failure if configured for monitoring. It will be appreciated that instead of providing the patient data 250 in a format which is ready to be used as input to the classifier, the mobile device 240 may also provide 'raw' patient data to the workstation, for example, the answers to the questionnaire. In such a case, the workstation may further pre-process the 'raw' patient data to obtain the patient data in the desired format. For example, the workstation may apply a rule-based system to the answers of the questionnaire to obtain the measurement data of a select health indicator.

The workstation 260 may represent an embodiment of the system 100 of FIG. 1. Alternatively, the mobile device 240 and the workstation 260 may together represent a distributed-type of embodiment of the system 100.

Computer Aided Diagnosis

FIG. 3 relates to the diagnosis of heart failure by means of a trained classifier and illustrates, for different scenarios, which set of health indicators may be used and the thereby obtained accuracy. In particular, a minimum set of health indicators is identified for the diagnosis of heart failure. This minimum set is well-suited to home diagnostic. The minimum set of health indicators may be extended, for example, by a GP, heart failure nurse, regular nurse, or other basic health-professional requesting a follow up assessment with one of the three following options to improve the diagnosis, for example via telemonitoring:

Home diagnostic+laboratory (in-vitro) tests
Home diagnostic+examination at GP clinic
Home diagnostic+laboratory tests+examination at GP clinic It will be appreciated that the minimum set of health indicators is well-suited for home diagnostic but may also be applied in a professional practice.

The table in FIG. 3 lists the selected health indicators which may be measured. Here, eGFR represents estimated glomerular filtration rate in ml/min. The eGFR may be measured directly through laboratory tests or calculated based on the so-called Modification of Diet in Renal Disease (MDRD) formula, which requires serum creatinine level in µmol/l, age, gender and ethnicity as follows:

$$eGFR = 32788 \times \text{Serum Creatinine}^{-1.154} \times \text{Age}^{-0.203} \times [1.210 \text{ if Black}] \times [0.742 \text{ if Female}]$$

With continued reference to FIG. 3, the beating frequency ('BFreq') may expressed as beats/min and may be measured manually, e.g., by counting or by a measurement device. For example, the beating frequency may be measured together with the oxygen saturation ('OxySat', in %) by, for example, a pulse oximeter device. Fatigue ('Fati') is commonly observed for patients with heart dysfunction and low cardiac output and may be measured through a questionnaire and quantified, e.g., as 'none', 'some' or 'severe' fatigue. Orthopnea ('OPNeu') represents fluid accumulation in the lungs when lying down, which eases off when a patient comes to an upright position. Typically, a patient would need several pillows to be able to sleep. Therefore, orthopnea may be evaluated and thereby measured based on a questionnaire which asks whether a patient uses pillows during night, and if so, how many. Dyspnea is a breathing frequency in breaths/min, which may be measured through a questionnaire, for example by asking the user to count the number of breaths during a predetermined period of time, e.g., 10 or 20 seconds, and asking the user to fill in the result. Pleura fluid ('PFluid') is a representative term for a range of sounds that can be distinguished on lung auscultation, and may be quantified for example as three levels: 1) dampened lower lung sounds, 2) pulmonary crackles and 3) dry, mostly nocturnal cough. Such lung auscultation requires physical examination that cannot be performed at home. Finally, gamma-glutamyl transpeptidase ('GGT'), which is a lab marker for liver congestion, may be measured by laboratory test and expressed in IU/l.

The classification of heart failure based on the select sets of health indicators of FIG. 3 has been clinically verified based in a clinical study that involved 159 patients, out of which 102 were healthy and 57 with heart failure. The data was acquired from hospitals. Initially, Recursive Feature Elimination (RFE) was performed on a full set of health indicators for five different classifiers: Support Vector Machines (SVM) with linear kernel, Logistic Regression, Random Forest, Gradient Boosting Machine and Stochastic Gradient Descent, with the Scikit-learn machine learning toolbox being used for each of the five classifiers. During training, Leave One Patient Out cross-validation was performed to improve assessment of the generalization of the classification.

As a result of the Recursive Feature Elimination applied to each classifier, a subset of the most relevant health indicators has been determined. Common health indicators for all classifiers are selected to represent a minimum subset of indicators in each of the above-mentioned scenarios. Classification by each of the classifiers, with only selected health indicators, is repeated to confirm their relevance in each of the scenarios. The accuracies which were obtained in each scenario, being a normalized average across all five different classifiers, was comparable to the accuracy obtained for the full set of health indicators (86.92%), confirming that the selected health indicators are indeed the most relevant.

With further reference to FIG. 2, the workstation 260 may receive numerical or other types of measurement values of any of the select sets of health indicators of FIG. 3. As already indicated, such measurement values may be obtained by laboratory test, answers to questionnaires, GP examination and/or measurement data obtained by the measurement device 210. The measurement values may be used as input to a classifier which was trained using, e.g., Support Vector Machines (SVM) with linear kernel, Logistic Regression, Random Forest, Gradient Boosting Machine or Stochastic Gradient Descent. The training of the classifier may be performed using the training data of N number of patients, preferably having a balanced number of patients with and without heart failure. This may avoid the classifier from being biased towards one class, which in turn may misclassify patients of the other class. During training, Leave One Patient Out cross-validation may be performed to improve assessment of the generalization of the classifier. Once a classifier has been trained, its relevant parameters may be saved and stored for future use. It is noted the training may be performed by the workstation 260 itself, but also by another entity, e.g., a workstation of a supplier of classification software.

Computer Aided Monitoring

FIG. 4 relates to the monitoring of heart failure by means of a trained classifier and illustrates, for different scenarios, which set of health indicators may be used and the thereby obtained accuracy. For such monitoring purposes, the degree of heart failure may be expressed on a scale of 1-5 indicating severity of the heart failure. Such a scale allows seeing an improvement (an increase) or an exacerbation (a decrease). It will be appreciated that the scale from 1-5 is one of many possible scales, but that a yes-no scale as outcome is less or not suited for monitoring since it cannot easily be interpreted as an exacerbation of a certain severity.

A minimum set of health indicators is identified for the monitoring of heart failure. This minimum set is well-suited to home monitoring. If there is uncertainty about the outcome of the home monitoring, the minimum set of health indicators may be extended, for example, by a GP, heart failure nurse, regular nurse, or other basic health-professional requesting, for example via telemonitoring, a follow up assessment with one of the three following options:

Home diagnostic+laboratory (in-vitro) tests
Home diagnostic+examination at GP clinic
Home diagnostic+laboratory tests+examination at GP clinic It will be appreciated that the minimum set of health indicators is well-suited for home monitoring but may also be applied in a professional practice.

The table in FIG. 4 lists the selected health indicators which may be measured. Reference is made to the description of FIG. 3 for the discussion and measurement of 'eGFR', 'Fati', 'Oxysat', 'OPNeu', 'Dyspnea' and 'PFluid'. Although described within the context of diagnosis of heart failure, their measurement values may also be indicative of a degree of heart failure, or specifically, changes in their measurement values may be indicative of a change in the degree of heart failure. Referring further to the other health indicators listed in FIG. 4, urea ('UR') is measured in mmol/l and may be obtained by laboratory tests. The urea level may be indicative of an exacerbation of heart failure as with such exacerbation, the kidney's level of hypoperfusion ("Renal hypoperfusion") may increase and the retention may go beyond what can be kept stable by the current medication dosage of the patient. Via a chain of neurohormonal processes, persistent renal hypoperfusion may also lead to a kidney injury, which manifests itself in a reduced glomerular filtration rate (eGFR) and/or elevated levels of creatinine and urea. With further reference to FIG. 4, heart murmur ('Hmu') refers to the following: in case of chronic volume overload, chances are that along with the geometric changes of the left heart, the mitral valve will no longer close properly and thus there will be a mitral valve insufficiency which may be detected by a heart sound/systolic murmur on auscultation. As such, the presence of such heart murmur may be indicative of an exacerbation of heart failure. Finally, jugular venous pressure may be a direct measure for the filling pressures of the right heart and therefore, right-sided heart failure or decompensation may be directly connected to distended neck veins ('prominent neck veins' or 'PNeckV' in FIG. 4). The size of such prominent neck veins may be measured in cm above sternal angle, which typically requires a physical examination of the patient.

The classification of the degree of heart failure based on the select sets of health indicators of FIG. 4 has been clinically verified based in a clinical study that involved 159 patients, out of which 83 had 'minimal heart failure', 9 had 'small heart failure', 10 had 'moderate heart failure', 18 had 'severe heart failure' and 39 had 'very severe heart failure'. The data was acquired from two hospitals—LUMC (Leiden, NL) and UMCU (Utrecht, NL). Recursive Feature Elimination (RFE) was performed on a full set of health indicators for five different classifiers: Support Vector Machines (SVM) with linear kernel, Logistic Regression, Random Forest, Gradient Boosting Machine and Stochastic Gradient Descent, using the Scikit-learn machine learning toolbox for each of the five classifiers. During training, Leave One Patient Out cross-validation was performed to improve generalization of the classification. As a result of the Recursive Feature Elimination applied to each classifier, a subset of the most relevant health indicators has been determined. Common health indicators for all classifiers are selected to represent a minimum subset of indicators in each of the above-mentioned scenarios. Classification by each of the classifiers, with only selected health indicators, is repeated to confirm their relevance in each of the scenarios. The accuracies which were obtained in each scenario, being a normalized average across all five different classifiers, was comparable to the accuracy obtained for the full set of health indicators (72.58%), confirming that the selected health indicators are indeed the most relevant.

The above monitoring of heart failure may be performed in a manner as described for diagnosis under "With further reference to FIG. 2", mutatis mutandis, with the exception that the training is preferably performed having balanced number of patients with different severities of heart failure (e.g., equal number of patients in each of five categories). This may avoid the classifier from being biased towards one class, which in turn may misclassify patients of the other classes. The graphical user interface may display the classification in form of a severity level of heart failure, for example, 'minimal heart failure', 'small heart failure', 'moderate heart failure', 'severe heart failure' or 'very severe heart failure'. The graphical user interface may also allow comparison with the degree of heart failure determined in the past.

With continued reference to both diagnosis and monitoring of heart failure, it is noted that classification of (the degree of) heart failure using a select set of health indicators and a classifier trained for said set may be applied in the area of cardiology, for example, at GP clinics, by heart failure nurses or by caregivers. Application in developing countries is envisaged where cardiology expertise is scarce. For patients that are monitored for various diseases, e.g., via telemonitoring, such monitoring may be easily extended to add such diagnosis for heart failure.

Figure 5:
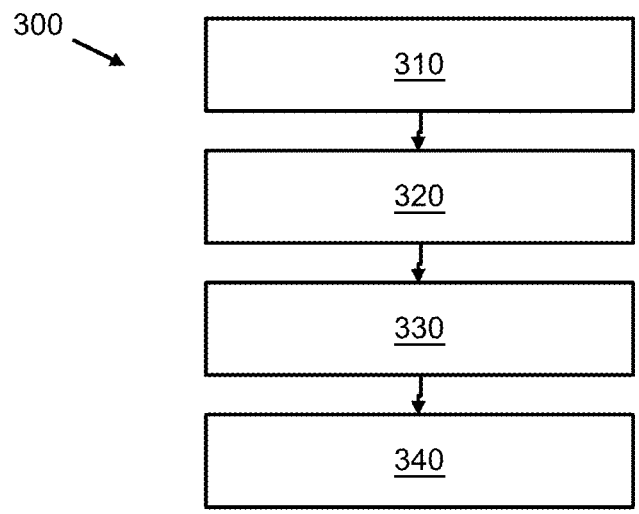
FIG. 5 shows a computer-implemented method for computer aided diagnosis or monitoring of heart failure patients.

FIG. 5 shows a computer-implemented method for computer aided diagnosis or monitoring of heart failure patients. It is noted that the method 300 may, but does not need to, correspond to an operation of the system, the mobile device or the workstation as described with reference to FIG. 1, 2 and others.

The method 300 comprises, in an operation titled "ACCESSING PATIENT DATA", accessing 310 patient data representing measurements of a select set of health indicators of a patient, the select set of health indicators comprising fatigue level of the patient, orthopnea of the patient, dyspnea of the patient, and oxygen saturation of the patient. The method 300 further comprises, in an operation titled "ACCESSING CLASSIFIER TRAINED ON TRAINING DATA", accessing 320 a classifier trained on training data, wherein each sample of the training data represents the measurements of the select set of health indicators of a studied patient and has a label indicating an occurrence or degree of heart failure of the studied patient. The method 300 further comprises, in an operation titled "APPLYING CLASSIFIER TO PATIENT DATA", applying 330 the classifier to the patient data to obtain a classification of the occurrence or degree of heart failure for the patient. The method 300 further comprises, in an operation titled "GENERATING OUTPUT DATA REPRESENTING CLASSIFICATION", generating 340 output data representing the classification. It will be appreciated that the above operation may be performed in any suitable order, e.g., consecutively, simultaneously, or a combination thereof, subject to, where applicable, a particular order being necessitated, e.g., by input/output relations. For example, the patient data and the classifier may be accessed simultaneously or in a different order as indicated above.

Figure 6:
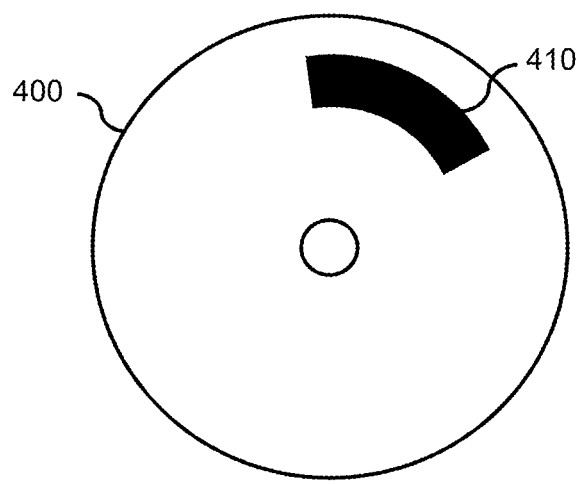
FIG. 6 shows a computer-readable medium comprising instructions.

The method 300 may be implemented on a computer as a computer implemented method, as dedicated hardware, or as a combination of both. As also illustrated in FIG. 6, instructions for the computer, e.g., executable code representing a computer program, may be stored on a computer readable medium 400, e.g., in the form of a series 410 of machine readable physical marks and/or as a series of elements having different electrical, e.g., magnetic, or optical properties or values. The executable code may be stored as transitory or non-transitory data. Examples of computer readable mediums include memory devices, optical storage devices, integrated circuits, servers, online software, etc. FIG. 6 shows an optical disc 400.

Additionally or alternatively, the computer readable medium 400 may store transitory or non-transitory data representing a classifier trained on training data and having as input measurements of a select set of health indicators of a patient and as output a label indicating an occurrence or degree of heart failure of the patient, the select set of health indicators comprising fatigue level, orthopnea, dyspnea and oxygen saturation of studied the patient. The data may be stored in the form of the series 410 of machine readable physical marks and/or as a series of elements having different electrical, e.g., magnetic, or optical properties or values.

Examples, embodiments or optional features, whether indicated as non-limiting or not, are not to be understood as limiting the invention as claimed.

It will be appreciated that the invention also applies to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing stage of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a data storage, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or stages other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for computer aided diagnosis or monitoring of heart failure patients, the system comprising:
   a memory comprising instruction data representing a set of instructions, and classifier data representing a trained classifier trained on training data in a patient population;
   a processor configured to communicate with the memory and to execute the set of instructions, wherein the set of instructions, when executed by the processor, cause the processor to:
      obtain a select set of health indicators from a large set of health indicators that are predictive of heart failure, the select set of health indicators consisting of fatigue level, orthopnea, dyspnea, and oxygen saturation;
      obtain patient data representing measurements of the select set of health indicators from a patient, so as to obtain patient fatigue level data, patient orthopnea data, patient dyspnea data and patient oxygen saturation data;
      provide a classification of an occurrence or degree of heart failure for the patient using the select set of health indicators and the trained classifier, wherein the measurements of the select set of health indicators from the patient are obtained in an outpatient setting, without any involvement or oversight by a medical expert or technician,
      retrieve the trained classifier from the memory, wherein each sample of the training data represents the measurements of the same select set of health indicators, consisting of fatigue level, orthopnea, dyspnea and oxygen saturation, of at least one studied patient in the patient population and has a label indicating an occurrence or degree of heart failure of the at least one studied patient, the training data including population fatigue level data, population orthopnea data, population dyspnea data, and population oxygen saturation data;
      wherein the patient data is different from the training data on which the trained classifier is trained,
      apply the trained classifier to the patient data, including the patient fatigue level data, the patient orthopnea data, the patient dyspnea data, and the patient oxygen saturation data, to obtain the classification of the occurrence or the degree of heart failure for the patient; and
      generate output data representing the classification of the occurrence or the degree of heart failure for the patient.

2. The system according to claim 1, further comprising:
   a user input interface configured to receive user input data from a user input device operable by a user; and
   a display output interface configured to provide the output data to a display to visualize output of the system,
   wherein the processor is configured to communicate with the user input interface and the display output interface, and
   wherein the set of instructions, when executed by the processor, cause the processor to:
      using the user input interface and the display output interface, establish a user interface which enables a user to provide information indicative of at least one of the fatigue level, the orthopnea and the dyspnea of the patient by providing answers to one or more onscreen questions;

using a rule-based system, determine a respective one of the measurement of the fatigue level, the measurement of the orthopnea and the measurement of the dyspnea of the patient based on the answers provided to the one or more onscreen questions.

3. The system according to claim 2, further comprising an interface to a measurement device for obtaining the measurement of the oxygen saturation of the patient.

4. The system according to claim 3, wherein the system is configured for computer aided diagnosis, and wherein the trained classifier is trained using the occurrence of heart failure as a label for each training sample.

5. The system according to claim 4, wherein the select set of health indicators further consists of a beating frequency of the patient.

6. The system according to claim 5, wherein the select set of health indicators is limited in size, and wherein the select set of health indicators is measured for the patient without the use of laboratory tests and/or without requiring examination by an expert at a hospital or at a General Practitioner's clinic.

7. The system according to claim 6, wherein the select set of health indicators, despite its small and limited size and lack of complexity of measurement, is configured to accurately provide the classification of the occurrence or the degree of heart failure for the patient.

8. The system according to claim 3, wherein the system is configured for computer aided monitoring, and wherein the trained classifier is trained using the degree of heart failure as a label for each training sample.

9. The system according to claim 2, wherein the rule-based system is configured to provide an interpretation of the answers to one or more onscreen questions and to translate the answers to one or more onscreen questions to the respective one of the measurement of the fatigue level, the measurement of the orthopnea, and the measurement of the dyspnea of the patient, and wherein the rule-based system includes heuristically designed rules or an expert system.

10. A workstation or server comprising the system according to claim 1.

11. The system according to claim 1, wherein the classification of the occurrence of heart failure for the patient includes a binary classification whether there is a 'heart failure' or there is 'no heart failure'.

12. The system according to claim 1, wherein the classification of the occurrence of heart failure for the patient is expressed as a likelihood of heart failure or confidence in the classification.

13. The system according to claim 1, wherein the classification of the degree of heart failure for the patient is expressed on a scale indicating severity of the heart failure.

14. The system according to claim 1, wherein the at least one studied patient includes two or more studied patients, and wherein the training of the trained classifier is performed using the training data of a balanced number of the two or more studied patients with and without heart failure.

15. The system according to claim 1, wherein the at least one studied patient includes two or more studied patients, and wherein of the trained classifier is trained using the training data of a balanced number of the two or more studied patients with different severities of heart failure.

16. The system according to claim 1, wherein the select set of health indicators is limited in size, and wherein the select set of health indicators is measured for the patient without the use of laboratory tests and/or without requiring examination by an expert at a hospital or at a General Practitioner's clinic.

17. The system according to claim 1, wherein the select set of health indicators, consisting of the fatigue level, the orthopnea, the dyspnea, and the oxygen saturation, despite its small and limited size and lack of complexity of measurement, is configured to accurately provide the classification of the occurrence or the degree of heart failure for the patient.

18. A non-transitory computer-readable medium storing computer readable instructions which, when executed by a processor system, cause the processor system to carry out operations for a computer aided diagnosis or monitoring of heart failure patients by:

obtaining a select set of health indicators from a large set of health indicators that are predictive of heart failure, the select set of health indicators consisting of fatigue level, orthopnea, dyspnea, and oxygen saturation;

accessing patient data representing measurements of the select set of health indicators, including fatigue level, orthopnea, dyspnea and oxygen saturation, from a patient, so as to obtain patient fatigue level data, patient orthopnea data, patient dyspnea data and patient oxygen saturation data;

providing a classification of an occurrence or degree of heart failure for the patient using a trained classifier trained on training data in a patient population, wherein the measurements of the select set of health indicators, including the patient fatigue level data, the patient orthopnea data, the patient dyspnea data, and the patient oxygen saturation data, from the patient are obtained in an outpatient setting, without any involvement or oversight by a medical expert or technician, accessing the trained classifier, wherein each sample of the training data represents the measurements of the same select set of health indicators, consisting of fatigue level, orthopnea, dyspnea and oxygen saturation, of at least one studied patient in the patient population and has a label indicating an occurrence or degree of heart failure of the at least one studied patient, the training data including population fatigue level data, population orthopnea data, population dyspnea data, and population oxygen saturation data;

wherein the patient data is different from the training data on which the trained classifier is trained;

applying the trained classifier to the patient data, including the patient fatigue level data, the patient orthopnea data, the patient dyspnea data, and the patient oxygen saturation data, to obtain the classification of the occurrence or the degree of heart failure for the patient; and generating output data representing the classification of the occurrence or the degree of heart failure for the patient.

* * * * *